US012774554B2

(12) United States Patent
Kang et al.

(10) Patent No.: US 12,774,554 B2
(45) Date of Patent: Oct. 27, 2026

(54) APPARATUS FOR TREATING LAUNDRY

(71) Applicant: LG Electronics Inc., Seoul (KR)

(72) Inventors: Hyemin Kang, Seoul (KR); Sanghun Bae, Seoul (KR)

(73) Assignee: LG Electronics Inc., Seoul (KR)

( * ) Notice: Subject to any disclaimer, the term of this patent is extended or adjusted under 35 U.S.C. 154(b) by 115 days.

(21) Appl. No.: 18/811,131

(22) Filed: Aug. 21, 2024

(65) Prior Publication Data

US 2025/0207320 A1 Jun. 26, 2025

(30) Foreign Application Priority Data

Dec. 22, 2023 (KR) ........................ 10-2023-0189285

(51) Int. Cl.
*D06F 73/02* (2006.01)
*A61L 2/07* (2006.01)
(Continued)

(52) U.S. Cl.
CPC ................ *D06F 73/02* (2013.01); *A61L 2/07* (2013.01); *A61L 2/26* (2013.01); *D06F 58/10* (2013.01);
(Continued)

(58) Field of Classification Search
CPC ........ D06F 73/02; D06F 58/10; D06F 58/203; A61L 2/07; A61L 2/26; A61L 2103/50;
(Continued)

(56) References Cited

U.S. PATENT DOCUMENTS

2002/0133969 A1* 9/2002 Cassella .................. D06F 58/10 34/201
2015/0020419 A1* 1/2015 Park ........................ D06F 58/10 38/3
(Continued)

FOREIGN PATENT DOCUMENTS

JP 2000-093698 A 4/2000
JP 2021-101785 A 7/2021
(Continued)

OTHER PUBLICATIONS

Office Action in Korean Appln. No. 10-2023-0189285, mailed on Sep. 24, 2025, 7 pages (with English translation).
(Continued)

*Primary Examiner* — Joseph L. Perrin
(74) *Attorney, Agent, or Firm* — Fish & Richardson P.C.

(57) ABSTRACT

An apparatus for treating laundry includes a cabinet having an opening at a front to put the laundry therethrough, a first case provided within the cabinet to mount the laundry, a second case rotatably coupled to the cabinet to open/close the opening and having an open surface in a front to put the laundry therethrough, a door rotatably coupled to the second case, and a machine room including a suction unit disposed under the first case to suck air inside the first case, a heat exchange unit disposed ahead of the suction unit to dry the sucked air, and a supply unit disposed ahead of the heat exchange unit to supply the air having passed through the heat exchange unit to the first case and the second case,
(Continued)

where the first case and the second case may be configured to be simultaneously supplied with the air from the supply unit.

14 Claims, 7 Drawing Sheets

(51) Int. Cl.

| | |
|---|---|
| ***A61L 2/26*** | (2006.01) |
| ***D06F 58/10*** | (2006.01) |
| ***D06F 58/20*** | (2006.01) |
| *A61L 103/50* | (2026.01) |

(52) U.S. Cl.
CPC ........ *D06F 58/203* (2013.01); *A61L 2103/50* (2026.01); *A61L 2202/11* (2013.01); *A61L 2202/121* (2013.01); *A61L 2202/122* (2013.01); *A61L 2202/15* (2013.01)

(58) Field of Classification Search
CPC ........... A61L 2202/11; A61L 2202/121; A61L 2202/122; A61L 2202/15
See application file for complete search history.

(56) References Cited

U.S. PATENT DOCUMENTS

| | | | | |
|---|---|---|---|---|
| 2016/0175471 | A1* | 6/2016 | Choi | D06F 73/02 239/58 |
| 2016/0208429 | A1* | 7/2016 | Park | D06F 71/02 |
| 2020/0080252 | A1* | 3/2020 | Lee | D06F 73/02 |
| 2021/0032797 | A1* | 2/2021 | Shin | D06F 67/005 |
| 2021/0054560 | A1* | 2/2021 | Kim | D06F 58/203 |
| 2021/0140095 | A1* | 5/2021 | Kim | D06F 71/34 |
| 2021/0156075 | A1* | 5/2021 | Song | D06F 58/44 |

FOREIGN PATENT DOCUMENTS

| | | | |
|---|---|---|---|
| KR | 10-2020-0013618 | A | 2/2020 |
| KR | 10-2020-0096478 | A | 8/2020 |
| KR | 10-2020-0116692 | A | 10/2020 |
| KR | 10-2021-0062398 | A | 5/2021 |

OTHER PUBLICATIONS

International Search Report and Written Opinion in International Appln. No. PCT/KR2024/010347, mailed on Nov. 4, 2024, 10 pages.

* cited by examiner

APPARATUS FOR TREATING LAUNDRY

CROSS-REFERENCE TO RELATED APPLICATIONS

Pursuant to 35 U.S.C. § 119(a), the present application claims the benefit of earlier filing date and right of priority to Korean Application No. 10-2023-0189285, filed on Dec. 22, 2023, the contents of which are hereby incorporated by reference herein in their entirety.

TECHNICAL FIELD

The present disclosure relates to an apparatus for treating laundry, and more particularly, to a laundry treating apparatus for performing a refresh cycle capable of performing at least one of deodorization, wrinkle removal, and sterilization of the laundry by supplying at least one of air and steam to the laundry.

BACKGROUND

A laundry treatment device refers to a device developed to wash and dry laundry at home and washhouse and to remove wrinkles on laundry. Classified as laundry treatment devices include a washing machine for washing laundry, a dryer for drying laundry, a washer/dryer with both washing and drying functions, a laundry management machine for refreshing laundry, steamer for removing wrinkles of laundry, etc.

Recently, a laundry treatment device corresponding to a laundry management device has appeared to allow laundry to be kept comfortable and clean without washing it with detergent by immersing them in water.

Such a conventional laundry treatment device has emerged to perform a refresh cycle of supplying either high-temperature air or steam to the laundry to deodorize the laundry, dry the laundry, and remove wrinkles of the laundry.

The laundry treatment device capable of performing the refresh cycle manages laundry by flowing the air and steam in a manner of supplying the air and steam from the rear and sucking the air and steam from the front. Refer to Korean Patent Publication No. 10-2020-0057545

The laundry treatment device of the related art has a problem in that laundry is damaged by managing different types of laundry at a time because an internal space supplied with air and steam is not partitioned.

SUMMARY

One object of the present disclosure is to provide a laundry treating apparatus having a second case for storing separate laundry.

Another object of the present disclosure is to provide a laundry treating apparatus having a machine room for simultaneously supplying air to a plurality of partitioned accommodation spaces.

Further object of the present disclosure is to provide a laundry treating apparatus for preventing steam from being supplied to an accommodation space of a second case.

To achieve these objects and other advantages and in accordance with the purpose of the disclosure, as embodied and broadly described herein, An apparatus for treating laundry according to the present disclosure may include an apparatus for treating laundry, the apparatus including a cabinet forming an exterior and having an opening formed in a front to put the laundry therethrough, a first case provided within the cabinet to mount the laundry put through the opening thereon, a second case rotatable coupled to the cabinet to open/close the opening and having an open surface in a front to put the laundry therethrough, a door rotatably coupled to the second case to open/close the open surface, and a machine room including a suction unit disposed under the first case to suck air inside the first case, a heat exchange unit disposed ahead of the suction unit to dry the sucked air at a high temperature, and a supply unit disposed ahead of the heat exchange unit to supply the air having passed through the heat exchange unit to the first case and the second case, wherein the first case and the second case may be configured to be simultaneously supplied with the air from the supply unit.

The first case may include a first supply hole communicating with the supply unit, the second case may include a second supply hole communicating with the supply unit, and the first supply hole and the second supply hole may be configured to face the supply unit.

The machine room may include a steam supply unit supplying steam, the steam supply unit including a water supply container detachably provided under the supply unit to store water, a steam generator accommodating a heater part generating steam from heating water supplied by communicating with the water supply container, and a steam nozzle located on a side of the supply unit and communicating with the steam generator to inject the steam generated by the steam generator, and the steam nozzle may be configured to supply the steam to the first case by being disposed behind the second case to face the first supply hole.

An area of the supply unit may increase upward.

The supply unit may include a partition partitioning the supply unit into a front and a rear to supply the air to the first supply hole and the second supply hole, respectively.

The first case may include a first communication hole perforating an upper surface of the first case and a discharge hole facing the suction unit and perforating a lower surface of the first case, the second case may include a second communication hole located above the upper surface of the first case to perforate a rear surface of the second case, and the apparatus may include a connection passage connecting the first communication hole and the second communication hole.

The air supplied through the second supply hole may be sucked into the suction unit by passing through the second communication hole, the connection passage, the first communication hole, and the discharge hole in order.

The air supplied through the first supply hole may pass through the discharge hole and to be sucked into the suction unit.

The second case may include a valve rotatably coupled to an outer surface of the second case to open/close the second communication hole and the valve may be larger than a width of the second communication hole.

The apparatus may include a hanger unit coupled to an upper surface of the first case to support a hanger having the laundry mounted thereon, the hanger unit extending from a rear of the first case toward a front to enable the laundry to face a front side.

Accordingly, the present disclosure may provide a laundry treating apparatus having a second case for storing separate laundry.

The present disclosure may provide a laundry treating apparatus having a machine room for simultaneously supplying air to a plurality of partitioned accommodation spaces.

The present disclosure may provide a laundry treating apparatus for preventing steam from being supplied to the accommodation space of the second case.

Additional scope of applicability of the present disclosure will become apparent from the following detailed description. However, since various changes and modifications within the spirit and scope of the present disclosure can be understood by those skilled in the art, it should be understood that specific embodiments, such as the detailed description and the preferred embodiments of the present disclosure, are given as examples.

DETAILED DESCRIPTION

Hereinafter, embodiments disclosed in the present specification will be described in detail with reference to the accompanying drawings. The present specification gives the same or similar reference numbers to the same or similar configurations even in different embodiments, and the description thereof is replaced with the initial description. Singular expressions used in the present specification include multiple expressions unless the context clearly indicates otherwise. In addition, in describing the embodiments disclosed in the present specification, if it is determined that a detailed description of related known techniques may obscure the gist of the embodiments disclosed in the present specification, the detailed description thereof will be omitted. In addition, it should be noted that the accompanying drawings are for the purpose of easily understanding the embodiments disclosed in the present specification, and the technical idea disclosed in the present specification should not be construed as limiting by the accompanying drawings.

Figure 1:
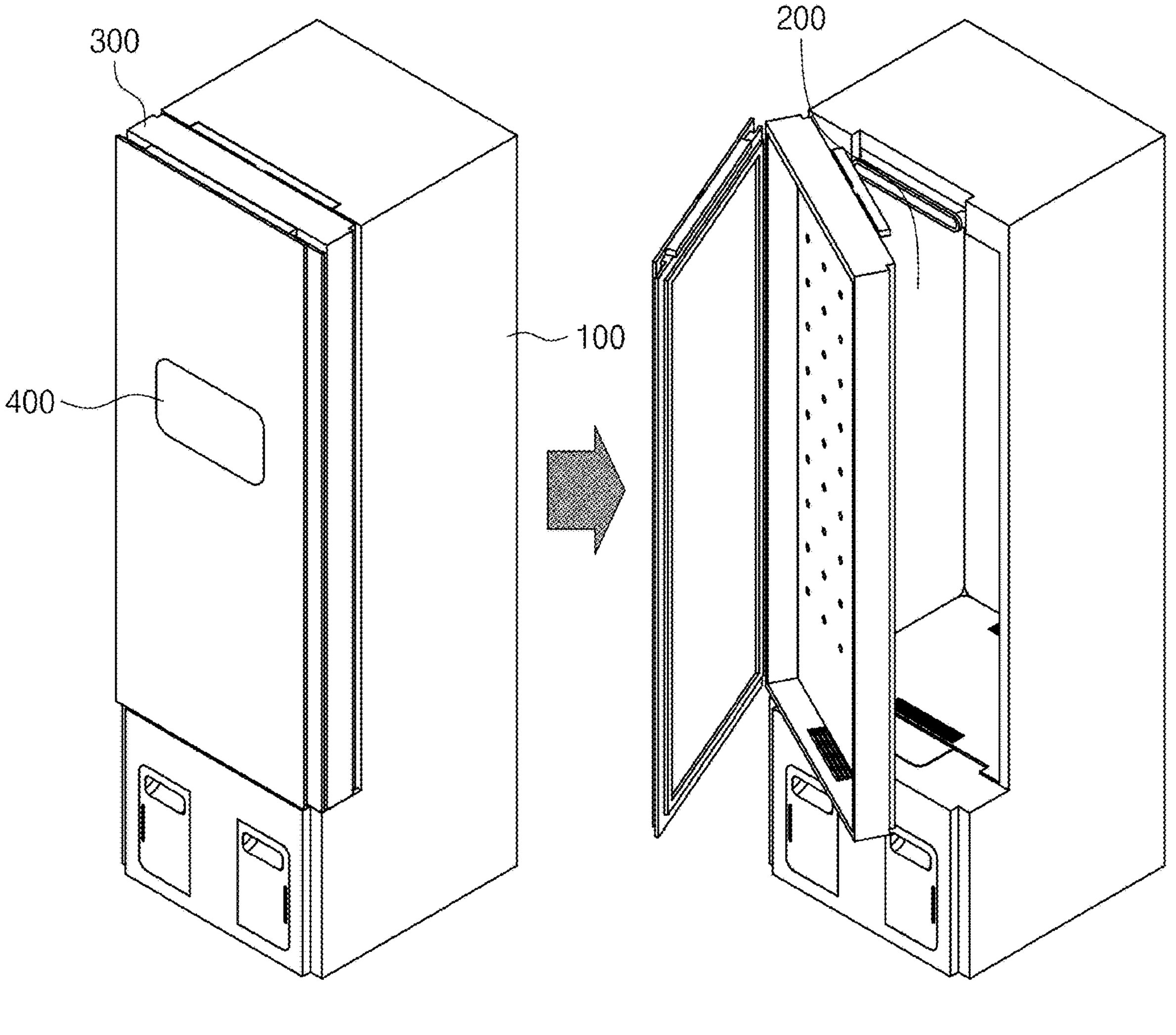
FIG. 1 is a diagram illustrating an appearance of a laundry treating apparatus having a second case part according to the present disclosure.

FIG. 1 illustrates an appearance of a laundry treating apparatus of the present disclosure.

Referring to FIG. 1, a cabinet 100 may form an exterior and include an opening, through which laundry is put, on a front side thereof. A first case 200 in which laundry put through the opening is accommodated may be provided inside the cabinet 100. The first case 200 may be formed of a plastic resin-based material, and may be formed of a reinforced plastic resin-based material that is not deformed by air having a temperature higher than that of air at room temperature or even heated air, steam, or moisture.

The first case 200 may have a height longer than a width. Accordingly, laundry may be accommodated in the first case 200 without being folded or wrinkled.

In addition, it may also include a second case 300 that is rotatably coupled to the cabinet 100 to open and close the opening and includes an open surface, in which laundry is put, on a front side.

Like the first case 200, the second case 300 may be formed of a plastic resin-based material, and may be provided as a reinforced plastic resin-based material that is not deformed by air at a temperature higher than that of air at room temperature or even heated air, steam, or moisture. It may also be provided in a shape corresponding to the first case. That is, it may be provided with a height greater than a width. Yet, the height of the second case may be greater than that of the first case, and the width of the second case may be greater than that of the first case. Accordingly, the first case 200 may be shielded by the second case 300.

In addition, a door may be rotatably coupled to the second case 300 and configured to open and close the open surface. That is, the second case may open and close the open surface of the first case 200, and the door may open and close the open surface of the second case.

In addition, the door may be provided long enough to open and close not only the open surface of the second case but also the open surface of the cabinet. Therefore, a machine room having a water supply container, a drain container, and the like provided under the second case may be covered. The machine room will be described later.

In addition, the door may be formed of a transparent material so that the inside of the second case is visible. Therefore, even when the second case is closed, the state of the laundry mounted in the second case may be checked.

Additionally, the laundry treating apparatus of the present disclosure may include a machine room 500 including a suction unit 510 disposed under the first case 200 and sucking air inside the first case 200, a heat exchange unit 520 disposed ahead of the suction unit and drying the sucked air into hot and dry air, and a supply unit 53 disposed ahead of the heat exchange unit and supplying the air having passed through the heat exchange unit to the first case and the second case above 300, and the first case and the second case may be provided to be simultaneously supplied with the air from the supply unit. The detailed structure will be described later.

Figure 2:
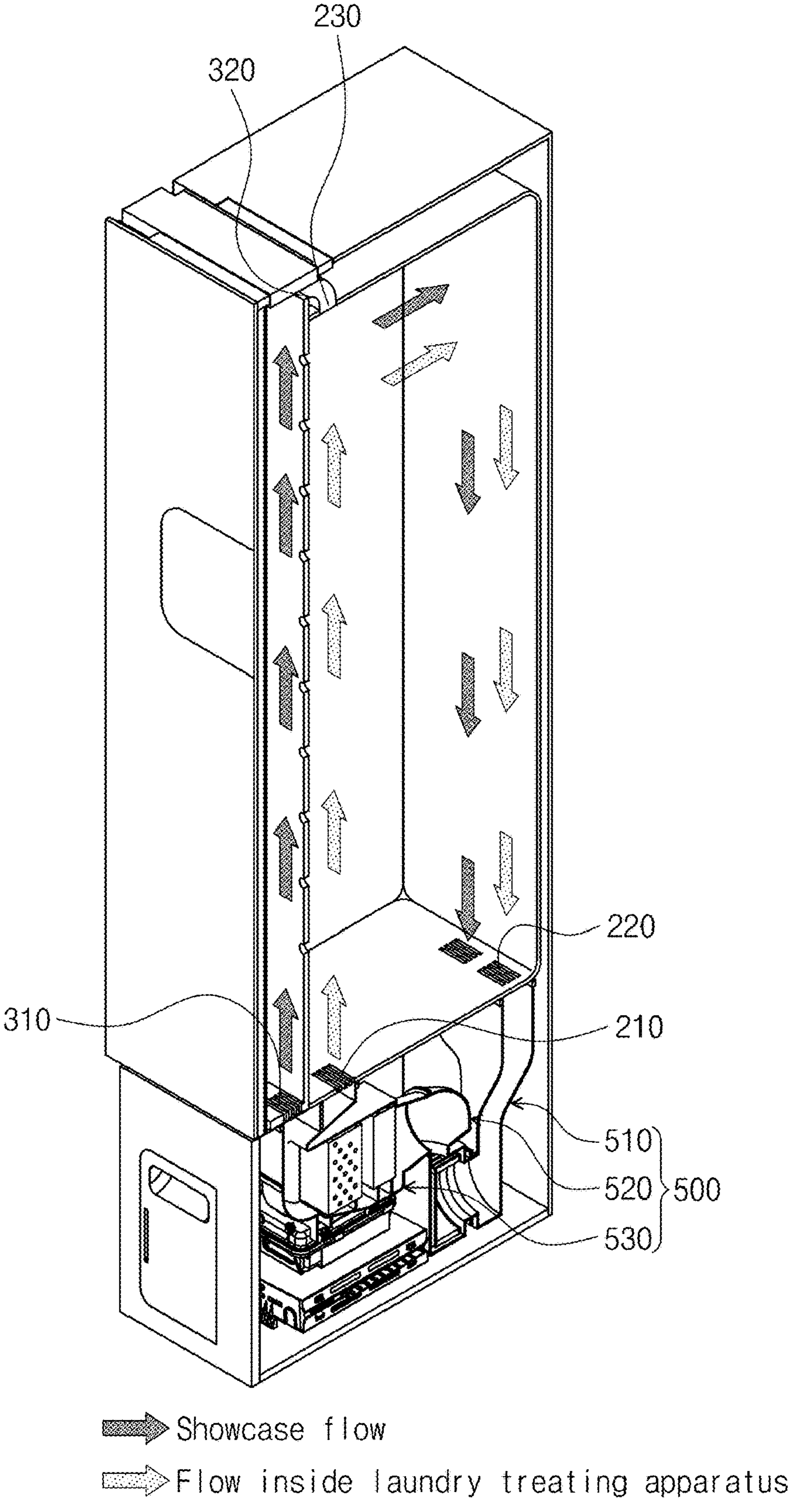
FIG. 2 is a diagram illustrating an internal air flow of a laundry treating apparatus according to the present disclosure.
Figure 3:
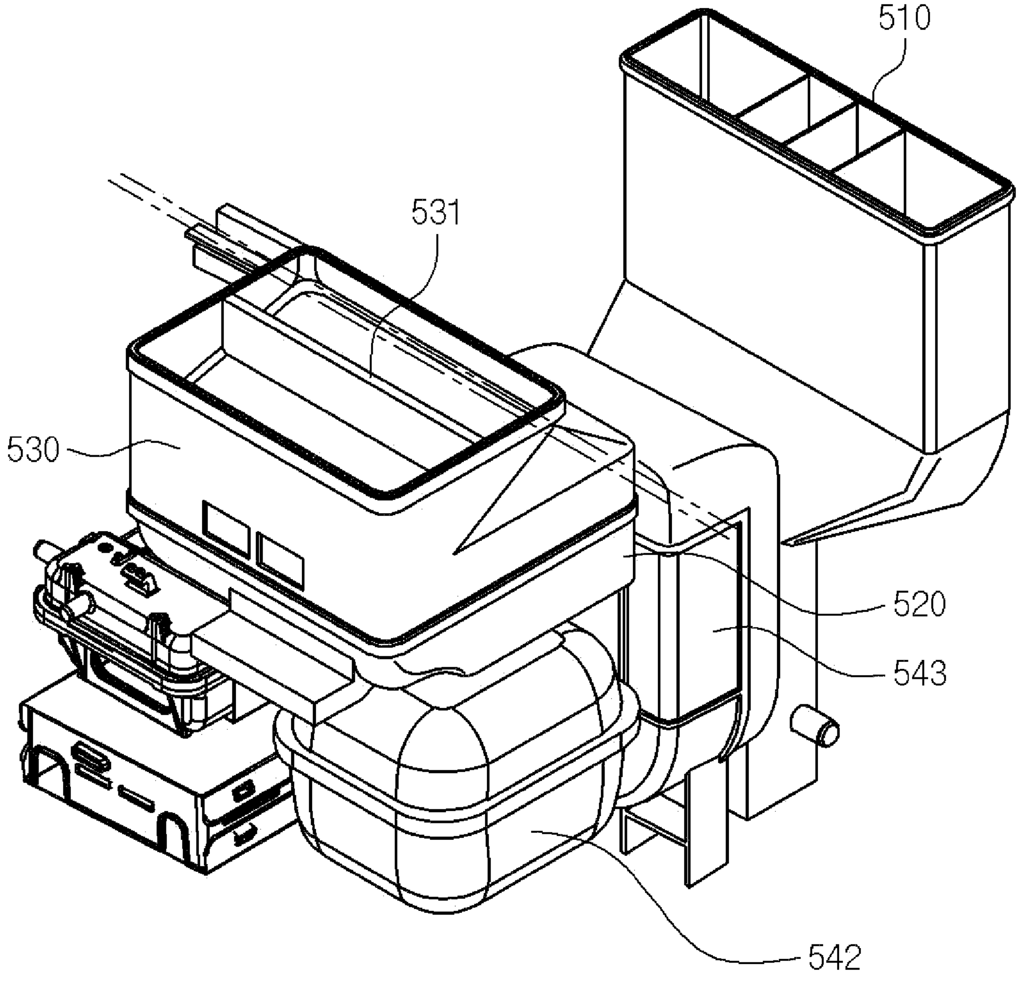
FIG. 3 is a diagram illustrating that air is supplied and sucked into the inside of a laundry treating apparatus from a machine room of the laundry treating apparatus according to the present disclosure.

FIGS. 2 and 3 illustrate that air flows inside the laundry treating apparatus of the present disclosure.

Referring to FIG. 2, the first case 200 may include a first supply hole 210 communicating with the supply unit 530. The first supply hole 210 may be provided to pass through a bottom surface of the first case.

In addition, the second case 300 may include a second supply hole 310 communicating with the supply unit 530. The second supply hole 310 may be provided to pass through a bottom surface of the second case.

The first supply hole 210 and the second supply hole 310 may be provided to face the supply unit 530. That is, the open surface of the supply unit may be provided to accommodate both the first supply hole and the second supply hole.

Therefore, high-temperature dry air discharged through the supply unit 530 may be divided and supplied to both of the first supply hole 210 and the second supply hole 310. Therefore, a single machine room 500 may simultaneously supply air to both the first case and the second case.

In addition, the first case 200 may include a first communication hole 230 perforating an upper surface of the first case. The air may be introduced from the second case through the first communication hole.

In addition, the first case 200 may include a discharge hole 220 facing the suction unit 510 and passing through a lower surface of the first case. The air flowing inside the first case may be sucked into the suction unit 510 through the discharge hole.

Since the first communication hole is provided in the upper surface of the first case and the discharge hole is provided on the bottom surface of the first case, the air may flow from the upper surface to the lower surface. For this reason, even when the laundry is hung toward the front, it is possible to increase an area in which the laundry and air are in contact with each other. In addition, since the upper surface of the cabinet 100 and the upper surface of the first case 200 may be provided to be spaced apart from each other, providing the first communication hole in the upper surface may facilitate installation of a connection passage that will be described later.

Meanwhile, the second case 300 may include a second communication hole 320 which is located above the upper surface of the first case 200 and passes through a rear surface of the second case. The air having passed through the second supply hole may move above the second case and may move to the inside of the first case through the second communication hole.

In addition, the second case 300 may include a connection passage 340 provided to connect the first communication hole and the second communication hole. The connection passage may be provided in a space between the cabinet 100 and the first case 200.

Furthermore, since the second case 300 is rotatably coupled to the cabinet above 100, a distance between the first communication hole 230 and the second communication hole above 320 increases when the second case is rotated to open the opening, so the connection passage above 340 may be provided in the form of a corrugated tube to shorten and lengthen the length thereof.

Since a pressure difference between the supply unit and the suction unit occurs due to a blowing fan provided between the suction unit 510 and the supply unit 530 in the machine room 500, the air may move from the suction unit to the supply unit.

Additionally, since the pressure of the first supply hole 210 and the second supply hole 310 is greater than that of the discharge hole 220, the air may move from the first supply hole and the second supply hole to the discharge hole.

The air supplied from the supply unit 530 through the second supply hole 310 moves upward in the second case 300, passes through the connection passage 340 via the second communication hole 320, and is then discharged from the first communication hole 230 to the first case 200. The air inside the first case may circulate in a manner of passing through the discharge hole 220, being sucked into the suction unit 510, passing through the heat exchange unit 520, and then moving toward the supply unit 530.

Likewise, the air supplied from the supply unit 530 through the first supply hole 210 may circulate in a manner of moving toward the upper surface of the first case 200, circulating inside the first case, passing through the discharge hole 220, being sucked into the suction unit 510, passing through the heat exchange unit 520, and then moving toward the supply unit 530.

Namely, the air discharged from the supply unit 530 may pass through the first supply hole 210 and the second supply hole 310 toward the first case 200 and the second case 300, and the air may be sucked back into the suction unit 510 through the discharge hole 220, pass through the heat exchange unit 520, and then flow toward the supply unit.

The above-described circulation may be performed by the blowing fan provided between the suction unit 510 and the supply unit 530.

FIG. 3 illustrates the machine room of the laundry treating apparatus of the present disclosure.

The machine room 500 may be disposed under the first case 200.

The machine room 500 may include the suction unit 510 for sucking the air inside the first case through the discharge hole 220, the heat exchange unit 520 disposed ahead of the suction unit to dry the sucked air at a high temperature, and the supply unit 530 disposed ahead of the heat exchange unit to supply the air having passed through the heat exchange unit to the first case 200 and the second case 300.

More specifically, the machine room 500 may be disposed in a manner of being separated or partitioned from the first case 200 and the second case 300 but communicating with the first case 200 and the second case 300.

The machine room 500 may be disposed under the first case 200 and the second case 300. Accordingly, when hot air having a small specific gravity is supplied to the first case 200 and the second case 300, it may be naturally supplied to laundry.

The machine room 500 may include the heat exchange unit 520 including a circulation duct for circulating the air inside the first case 200 and the second case 300 and a plurality of heat exchangers disposed on the circulation duct to cool and condense the air and heat the air.

The machine room 500 may include a heat pump system having a compressor connected to a plurality of the heat exchangers to compress a refrigerant that cools or heats the air.

In addition, a blowing fan for flowing the air may be provided.

Meanwhile, the machine room 500 may include a steam supply unit capable of supplying steam to the inside of the first case 200.

The steam supply unit may be provided to generate the steam by heating water. Accordingly, the laundry accommodated in the first case is exposed to hot air and steam, so that deodorization, sterilization, and wrinkle removal may be performed thereon.

The steam supply unit may include a water supply container located below the supply unit and detachably provided to store water therein, a steam generator 542 accommodating a heater part generating steam by communicating with the water supply container, being supplied with the water, and heating the supplied water, and a steam nozzle 543 communicating with the steam generator and located on a side of the supply unit to inject the steam generated by the steam generator.

In addition, it may include a drain tank that collects condensed water in the process of dehumidifying the air that is passing through the heat exchange unit.

The water supply container and the drain tank may be detachably provided under the supply unit 530. Thus, even if the laundry treating apparatus of the present disclosure is not disposed near a water supply source or a sewer, a user may detach and transport the water supply container and the drain tank whenever necessary.

The water supply container and the drain tank may be disposed side by side along a width direction of the machine room 500.

In addition, the machine room 500 may further include a drawer configured to accommodate articles necessary for managing the laundry. The drawer may be configured to be pulled out of the machine room 500 and include a space for accommodating articles such as an iron and the like therein.

Meanwhile, the supply unit 530 may be provided so that an area thereof increases upward. As the area of the supply unit increases upward, it may be easy to simultaneously supply the air to the first supply hole 210 and the second supply hole 310.

Additionally, the supply unit 530 may include a partition 531 provided to divide the supply unit into a front and a rear to facilitate the supply of the air into the first supply hole 210 and the second supply hole 310.

That is, the air toward the rear of the partition based on the partition 531 may be supplied to the first case 200 through the first supply hole 210, and the air toward the front of the partition may be supplied to the second case 300 through the second supply hole 310.

It is preferable that the partition 531 is provided at a position corresponding to a boundary between the second case 300 and the first case 200.

The partition 531 may be formed of the same material as the supply unit 530, but may be formed of a plastic resin-based material, and may be formed of a reinforced plastic resin-based material that is not deformed by air having a temperature higher than that of air at room temperature, heated air, steam, or moisture.

Figure 4:
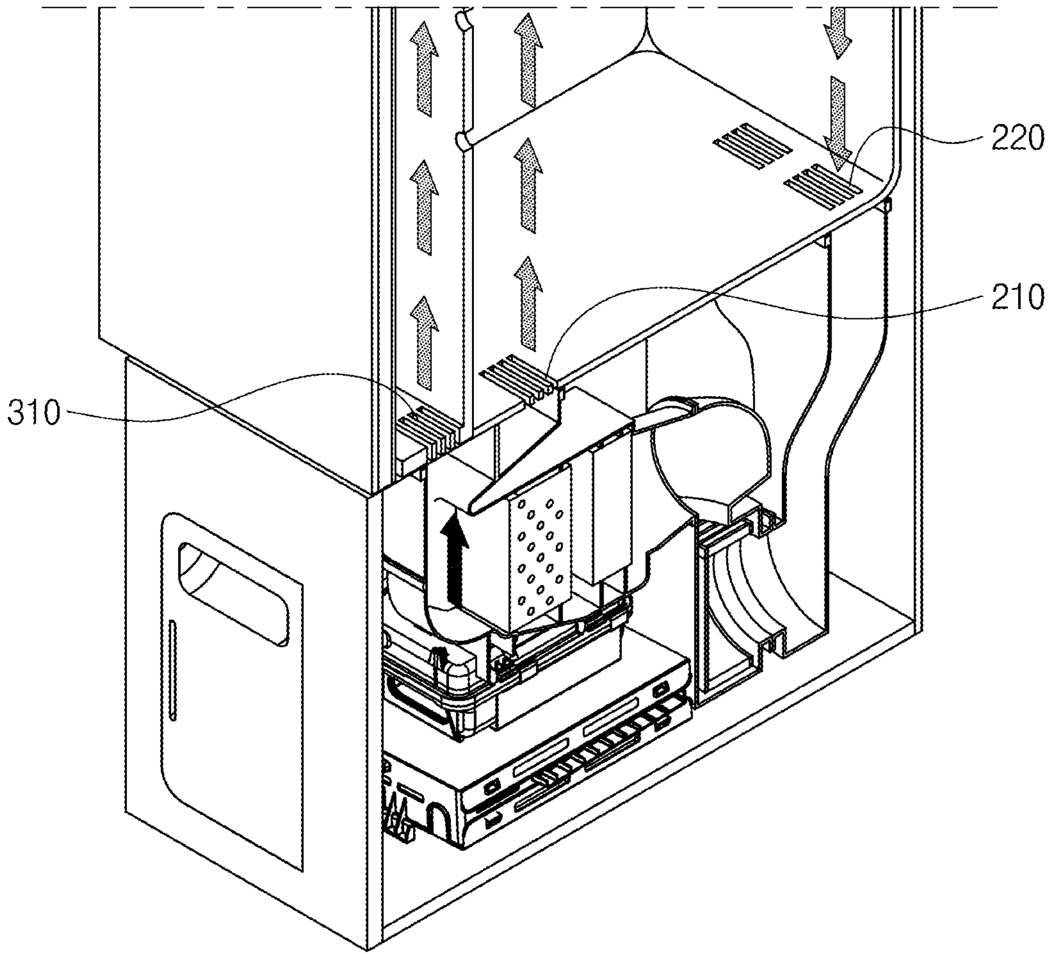
FIG. 4 is a diagram illustrating a machine room of a laundry treating apparatus of the present disclosure.

FIG. 4 illustrates a process in which the air supplied to the second case 300 through the second supply hole 310 is sucked into the suction unit 510 through the first case 200 and a process in which the air supplied to the first case 200 through the first supply hole 210 is sucked into the suction unit 510.

The air supplied from the supply unit 530 to the second case 300 through the second supply hole 310 may move upward in the second case, pass through the second communication hole 320, and head to the first case 200 through the connection passage 340.

In addition, the air may be supplied from the supply unit 530 to the first case above 200 through the first supply hole 210.

Therefore, all air supplied from the above supply unit 530 is directed to the inside of the first case 200, and may be sucked into the suction unit 510 through the discharge hole 220 provided in the first case to circulate.

Figure 5:
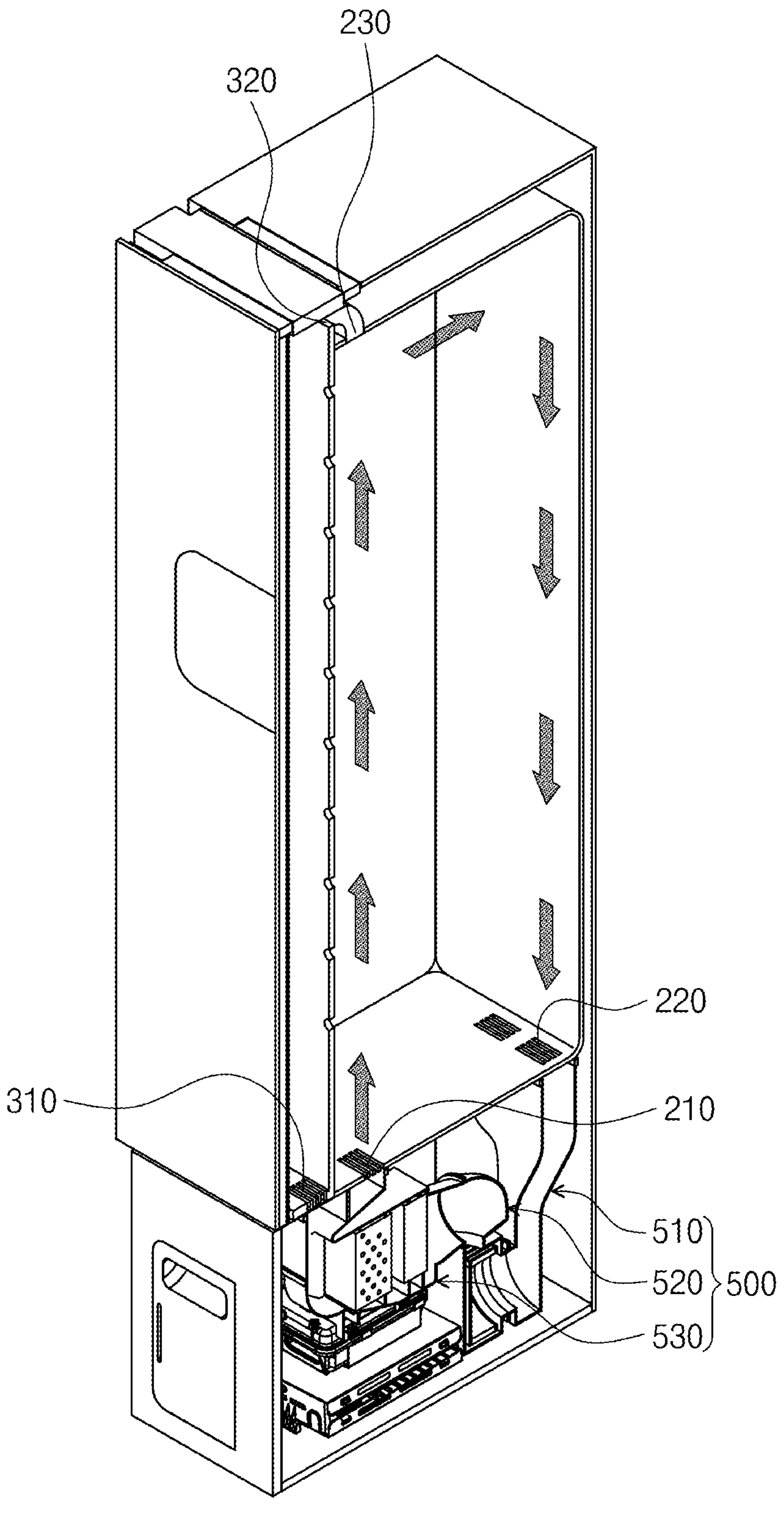
FIG. 5 is a diagram illustrating the flow of air from a second case to a first case of a laundry treating apparatus of present disclosure.

FIG. 5 illustrates that the flow of air is controlled by a valve provided to the second case in the laundry treating apparatus of the present disclosure.

The second case 300 may include a valve rotatably coupled to an outer surface of the second case to open and close the second communication hole 320. The valve may be rotatably coupled to an outer surface of a rear surface of the second case.

Therefore, the valve 330 may be rotated by the air from the second case 300 to the first case 200, and thus the second communication hole 320 may be opened. The second communication hole may be closed by the valve if the air is not supplied.

On the contrary, the valve may be provided to have a width wider than that of the second communication hole 320 in order to prevent the valve from being rotated into the inside of the second communication hole by the rear surface of the second case 300. Therefore, the valve may be rotated into the inside of the second communication hole by the air or steam supported by an outer circumferential surface of the second communication hole and directed from the first case 200 to the second case 300, and thus the second communication hole may not be opened. Accordingly, the second communication hole may be shielded.

That is, the valve 330 allows air to move from the second case 300 to the first case 200, but may block air or steam from moving from the first case 200 to the second case 300. However, in this case, the connection passage 340 should be provided larger than the area of the valve.

Meanwhile, a controller for controlling a motor connected to the valve may be provided to control the flow of the air.

The valve corresponds to one embodiment, and any configuration may be used as long as it allows air to move only in one direction.

Figure 6:
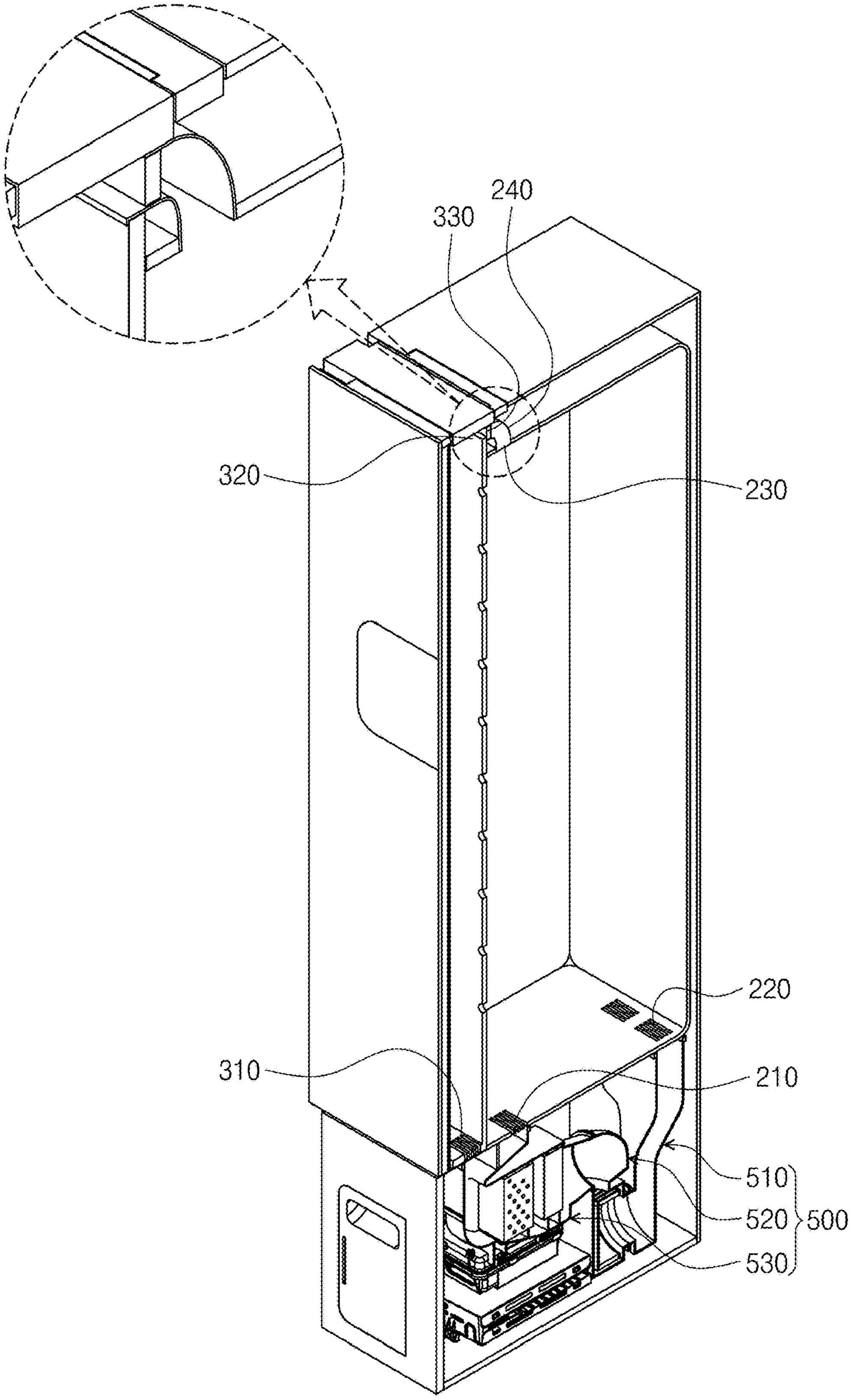
FIG. 6 is a diagram illustrating that steam is supplied from a steam supply unit of a laundry treating apparatus of the present disclosure.

FIG. 6 illustrates that the steam supplied from the steam supply unit flows.

The steam nozzle of the laundry treating apparatus according to the present disclosure may be positioned behind the second case and provided to face the first supply hole to supply steam to the first case.

Products sensitive to moisture may be provided in the second case 300. Therefore, it may be necessary to cut off the supply of steam to the second case.

Accordingly, the steam nozzle 543 of the laundry treating apparatus of the present disclosure may be provided in the machine room 500 so as not to communicate with the second supply hole 310 but to communicate only with the first supply hole 210. That is, it may be provided on a side surface of the supply unit 530, and closer to the first case at a boundary between the second case 300 and the first case 200. Also, it may be located behind the partition 531.

Therefore, the steam discharged through the steam nozzle 543 may be supplied to the first case 200 through the second supply hole 310.

Furthermore, when the steam is supplied, air may not be supplied from the supply unit 530. Accordingly, the valve 330 shields the second communication hole 320 and cannot move to the second case through the second communication hole because the valve is not rotated by the steam.

Therefore, the steam flowing inside the first case 200 may be sucked into the suction unit 510 through the discharge hole 220.

Figure 7:
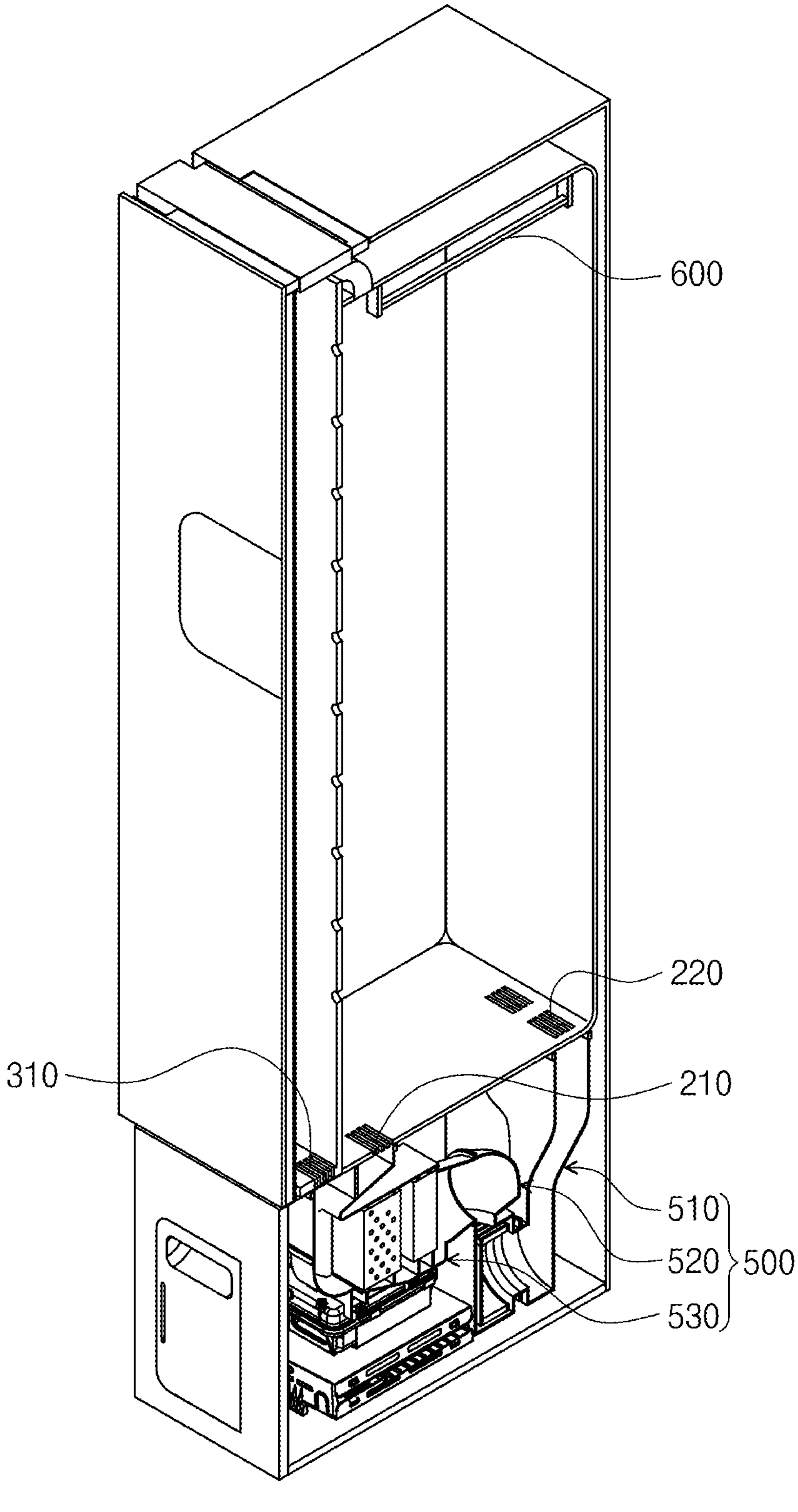
FIG. 7 is a diagram illustrating a direction of a hanger unit of the laundry treating apparatus according to the present disclosure.

FIG. 7 illustrates a hanger unit on which laundry are mounted in the laundry treating apparatus of the present disclosure.

The laundry treating apparatus of the present disclosure may include a hanger unit 600 coupled to an upper surface of the first case to support a hanger on which laundry is mounted. When the laundry is mounted on the hanger unit 600, the laundry may be disposed in a state of being suspended in the air in the first case 200.

Since the laundry treating apparatus of the present disclosure includes the second case 300, it may be necessary to allow the laundry to face forward in order to maintain an amount of the mounted laundry while making the length of the cabinet 100 in the front-rear direction the same as that of the laundry treatment device of the related art. Therefore, the hanger unit 600 may extend from the rear of the first case 200 to the front.

Since the laundry is set to face the front, if the air supplied from the supply unit 530 faces from the front to the rear, the air may not flow smoothly.

Accordingly, the laundry treating apparatus of the present disclosure may guide the air moving from the second case 300 to the first case to move from the top to the bottom by providing the first communication hole 230 in the upper surface of the first case 200. Accordingly, a contact area between the laundry and the air is increased, and air may flow smoothly.

Since the present disclosure may be modified and implemented in various forms, the scope of the rights is not limited to the above-described embodiments. Therefore, if the modified embodiment includes components of the claims of the present disclosure, it should be construed as pertaining to the scope of the rights of the present disclosure.

What is claimed is:

1. An apparatus for treating laundry, the apparatus comprising:

a cabinet defining an exterior of the apparatus, the cabinet having an opening defined at a front of the cabinet and configured to receive the laundry therethrough;

a first case provided within the cabinet, the first case being configured to receive the laundry;

a second case rotatably coupled to the cabinet, the second case being configured to open and close the opening and having an open surface defined at a front of the second case and configured to receive laundry therethrough;

a door rotatably coupled to the second case, the door being configured to open and close the open surface; and a machine room comprising:

a suction unit disposed under the first case, the suction unit being configured to draw air from an interior of the first case, a heat exchange unit disposed forward relative to the suction unit, the heat exchange unit being configured to dry the air drawn from the interior of the first case; and a supply unit disposed forward relative to the heat exchange unit, the supply unit being configured to supply the air that has passed through the heat exchange unit to the first case and the second case, wherein the first case comprises a first supply hole communicating with the supply unit and facing an upper direction, and wherein the second case comprises a second supply hole communicating with the supply unit and facing the upper direction, and wherein the supply unit is configured to, based on both the first supply hole and the second supply hole facing the upper direction, supply air simultaneously to the first case and the second case.

2. The apparatus of claim 1, wherein the first supply hole and the second supply hole are configured to face the supply unit.

3. The apparatus of claim 2, wherein the machine room comprises a steam supply unit supplying steam, the steam supply unit comprising:

a water supply container detachably provided under the supply unit, the water supply container being configured to store water;

a steam generator configured to accommodate a heater, the steam generator being configured to generate steam based on heating the water supplied by the water supply container; and a steam nozzle located on a side of the supply unit and in communication with the steam generator, the steam nozzle being configured to inject the steam generated by the steam generator, wherein the steam nozzle is configured to supply the steam to the first case based on the steam nozzle being disposed behind the second case to face the first supply hole.

4. The apparatus of claim 2, wherein an area of the supply unit increases upward.

5. The apparatus of claim 4, wherein the supply unit comprises a partition that partitions the supply unit into a front portion and a rear portion to supply the air to the first supply hole and the second supply hole, respectively.

6. The apparatus of claim 3, wherein the first case comprises a first communication hole perforating an upper surface of the first case and a discharge hole facing the suction unit and perforating a lower surface of the first case, wherein the second case comprises a second communication hole located above the upper surface of the first case to perforate a rear surface of the second case, and wherein the apparatus comprises a connection passage connecting the first communication hole and the second communication hole.

7. The apparatus of claim 6, wherein the suction unit is configured to draw air supplied through the second supply hole based on the air passing through the second communication hole, the connection passage, the first communication hole, and the discharge hole in order.

8. The apparatus of claim 6, wherein the suction unit is configured to draw the air supplied through the first supply hole, the air passing through the discharge hole and then being drawn into the suction unit.

9. The apparatus of claim 6, wherein the second case comprises a valve rotatably coupled to an outer surface of the second case, the valve being configured to open and close the second communication hole, and wherein the valve is larger than a width of the second communication hole.

10. The apparatus of claim 1, further comprising a hanger unit coupled to an upper surface of the first case and configured to support a hanger having the laundry mounted thereon, the hanger unit extending from a rear of the first case toward a front to enable the laundry to face a front side.

11. The apparatus of claim 1, wherein the door is made of a transparent material that provides visibility of an interior of the second case.

12. The apparatus of claim 1, wherein the first supply hole and the second supply hole are defined at a same vertical level relative to a bottom of the machine room.

13. The apparatus of claim 1, wherein the supply unit defines an open surface that surrounds both the first supply hole and the second supply.

14. The apparatus of claim 13, wherein the supply unit comprises a partition that partitions the open surface into a front portion and a rear portion and is configured to supply the air to the first supply hole and the second supply hole, respectively.

* * * * *